United States Patent
Gagné et al.

(10) Patent No.: US 6,385,019 B1
(45) Date of Patent: May 7, 2002

(54) COMPENSATION OF DIFFERENTIAL FLOATING CAPACITANCE BETWEEN DUAL MICROELECTRODES

(75) Inventors: Simon Gagné, St-Antoine-de-Tilly; Jdaya Ganguly, Ste-Foy; Sylvain Comtois, Quebec, all of (CA)

(73) Assignee: Université Laval, Québec (CA)

( * ) Notice: Subject to any disclaimer, the term of this patent is extended or adjusted under 35 U.S.C. 154(b) by 0 days.

(21) Appl. No.: 09/318,127

(22) Filed: May 25, 1999

Related U.S. Application Data
(60) Provisional application No. 60/086,710, filed on May 26, 1998.

(51) Int. Cl.[7] ............................. H01G 2/00; A61B 5/00
(52) U.S. Cl. ............................ 361/15; 361/58; 361/115
(58) Field of Search ............................. 361/15, 90, 58, 361/115

(56) References Cited

U.S. PATENT DOCUMENTS

| | | | |
|---|---|---|---|
| 5,981,268 A | * 11/1999 | Kovacs et al. | 435/287.1 |
| 6,163,719 A | * 12/2000 | Sherman | 600/547 |

OTHER PUBLICATIONS

Ganguly, U. S. On indcutor simulation reactive twopole synthesis with all pass and related transfos. Proceedings IEEE, 67, pp. 319–321, 1979.

Schanne, O. F., Lavallée, M., Laprade, R., Gagné, S. Electrical properties of glass microelectrodes. Proceedings IEEE, 56, pp. 1072–1082, 1968.

Guld., C. Cathode follower and negative capacitance as high input circuits. Proceedings IRE, 50, pp. 1912–1927, 1962.

Axon (The) Guide. Axon Instruments, Inc. 1101 Chess Drive, Foster City, CA 94404 USA. Instrumentation for measuring bioelectric signals, chapter 3, pp. 25–80, 1993.

Kootsey, J. M., Johnson, E. A. Buffer amplifier with femtofarad capacity using operational amplifiers, Proceedings IEEE Trans. on Biomed. Eng., BME–20, pp. 389–391, 1973.

Gagné, S., Poussart, D. Recordings of bioelectric potentials with glass microlectrodes: limitations of unity–gain follower with buffer. Proceedings IEEE Trans. on Biomed. Eng. BME–23, pp. 81–83, 1976.

Axoprobe–1A manual. Axon Instruments, Inc. 1101 Chess Drive, Foster City, Ca 94404 USA. $C_x$ Comp, pp. E–14 to E–16, 1988.

* cited by examiner

Primary Examiner—Stephen W. Jackson
(74) Attorney, Agent, or Firm—Oglivy Renault; James Anglehart (57) ABSTRACT

A circuit and a method for compensating the floating differential capacitance appearing between two recording microelectrodes is presented. It is shown how this floating capacitance can be neutralized so that current in any microelectrode can be injected without any significant cross-talk picked up by the other. It is a fully symmetrical compensation.

12 Claims, 7 Drawing Sheets

COMPENSATION OF DIFFERENTIAL FLOATING CAPACITANCE BETWEEN DUAL MICROELECTRODES

This appln claims benefit of Prov. No. 60/086,710 filed May 26, 1998.

FIELD OF THE INVENTION

This invention relates to recording microelectrodes used for biological readings. In particular, it relates to a circuit and a method for compensating the floating differential capacitance appearing between the microelectrodes.

BACKGROUND OF THE INVENTION

Faithful recording of biological signals with a single glass microelectrode cannot usually be done without compensating the undesired capacitances at the microelectrode boundaries with a negative capacitance created across the microelectrode by a negative impedance converter. Among the main undesired capacitances are the intrinsic input amplifier capacitance and a capacitance proportional to the length of the leads connecting the microelectrode to the amplifier and guards, used for shielding the microelectrode from external noise. Microelectrodes are used to measure electrical potentials on organisms such as humans, animals or even plants. Microelectrodes are able to pick up the small voltage fluctuations that arise from muscle, brain or neural activity. It is well known in the art how to apply such microelectrodes to an organism.

Not always negligible is a capacitance located at the tip of the microelectrode, which adds another small (or the order of a few pF) capacitance for each "mm" length of tip immersed in the preparation. Several methods have been developed for compensating these capacitance effects in order to achieve a desirable response of the recording system. A sophisticated technique for avoiding capacitive negative compensation is a follower with a buffer. It succeeds in reducing a large part of input capacitance by bootstrapping the amplifier head stage, but it does not always achieve full compensation because of the distributed nature of the microelectrode's electrical parameters. Recording with two microelectrodes is more complicated because a differential floating capacitance appears between them, which cannot be compensated with existing grounded microelectrode capacitance neutralization circuits. There is then a need for compensating the floating differential capacitance.

Recording with two microelectrodes is desirable in many experimental procedures. When transient phenomena are not important, no special procedure is required and the experimenter can ignore any transient phenomenon and just look at steady state signals. Quite often though, experiments with two microelectrodes are designed for looking at short time effects, for example, injecting a current with one microelectrode and looking at the same time at the change reflected on the other recording microelectrode. A circuit (Axoprobe-1A from Axon Instruments Inc.) is already available commercially for compensating the effect of injecting a current in one microelectrode without seeing its effect on the recording microelectrode. However, this circuit is not symmetrical as it operates on one side only. One microelectrode is for recording and the other is for injecting current. Microelectrode roles cannot be switched.

Figure 1:
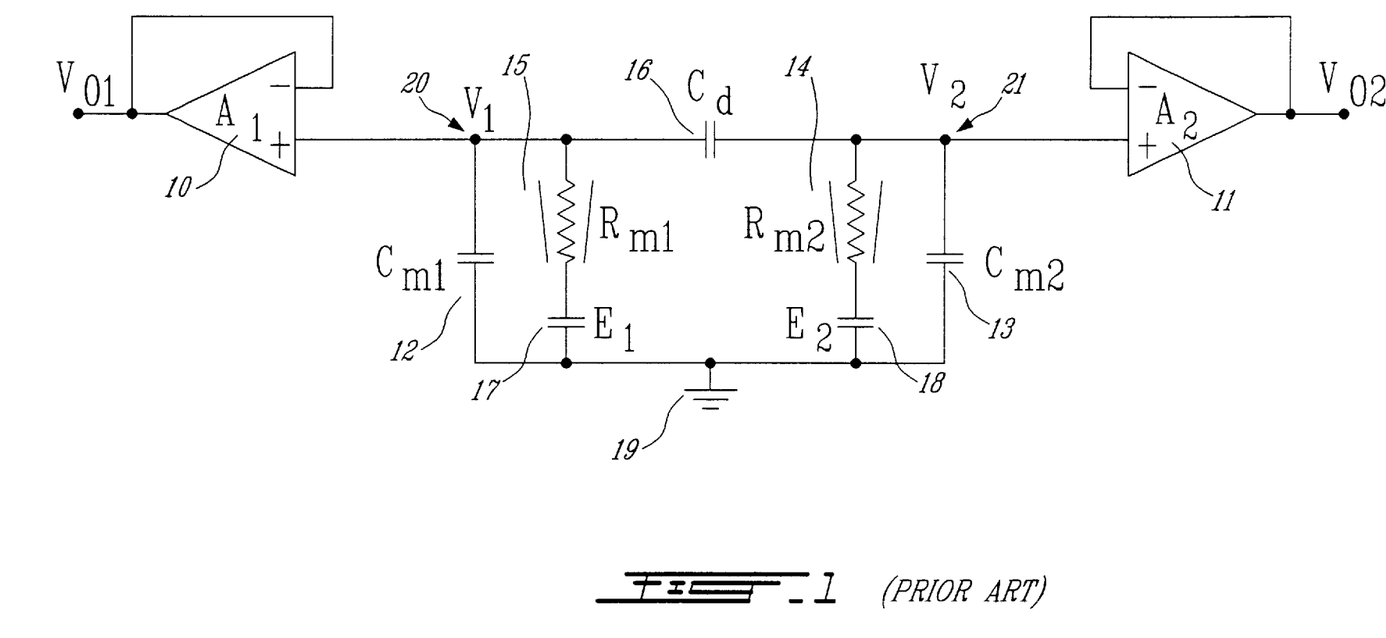
FIG. 1 illustrates a prior art electrical circuit having two microelectrodes recording signals $E_1$ and $E_2$ from their respective follower amplifier and showing the stray capacitances (two common mode capacitances and one differential mode capacitance)

FIG. 1, labeled as prior art, depicts a typical experimental set up when recording with two microelectrodes. It can be seen that two microelectrodes 15 and 14 ($R_{m1}$ and $R_{m2}$), each recording their own intra-cellular potential 17 and 18 ($E_1$ and $E_2$), are connected to their respective follower amplifier 10 and 11 ($A_1$ and $A_2$). As explained earlier, each microelectrode and amplifier contributes to the grounded capacitance 12 and 13 ($C_{m1}$ and $C_{m2}$) appearing across each microelectrode. These capacitances can be compensated provided a negative capacitance is generated as input impedance of the associated compensating circuit. However, due to the fact that the two microelectrodes are close together, another floating stray capacitance of differential nature 16 ($C_d$) appears between them. The value of this capacitance is dependent on the distance between the two microelectrodes, on the nature of the glass and most importantly on the length of the tips joined together at the end. It can be shown that this capacitance cannot be cancelled out with either amplifier compensating circuit. The cross-talk effect of this capacitance can corrupt the recording signals. In fact, any signal appearing on one microelectrode is also partially seen by the other through this differential capacitance. Since the quality of the readings is essential in many applications, compensating for this differential capacitance is important to ensure good interpretation of the results. Reproducing physiological signals with high fidelity is necessary for today's medical world.

SUMMARY OF THE INVENTION

One aim of this invention is to provide a circuit and a method for compensating the differential floating capacitance between dual microelectrodes.

Another object of this invention is to permit a better reproduction of physiological signals when measuring with dual microelectrodes.

In accordance with the present invention, there is provided a method for processing signals from two microelectrodes to neutralize a floating differential capacitance that appears between the two electrodes. Readings of the potential at two points on an organism are taken. A differential amplifier is provided and connected to the two reading points. By adjusting an element of the differential amplifier, it is possible to cancel out the floating differential capacitance.

The differential amplifier can be composed of two amplifiers interconnected by an adjustable resistive element. When connecting the differential amplifier to the reading points, two capacitors can be introduced in the connection. Adjusting an element of the differential amplifier can consist in adjusting a resistive element in the differential amplifier. In order to cancel the floating differential capacitance, the output signals of the microelectrodes can by analyzed in different ways. For example, they can be displayed on an oscilloscope and an operator can adjust the element or the waveforms can be analyzed automatically and an adjustment can be provided.

In accordance with another broad aspect of the invention, a system is provided for synthesizing a negative floating capacitance matching a floating differential capacitance appearing between two microelectrodes. This system comprises two amplifiers connected to the two microelectrodes. It also comprises an adjustment circuit element interconnecting the negative inputs of these two amplifiers and the outputs of these amplifiers are fed-back to the microelectrodes. The outputs of the microelectrodes can be provided with followers amplifiers. The adjustment circuit element can be a variable resistive element and the amplifiers can be connected to capacitive elements.

BRIEF DESCRIPTION OF THE DRAWINGS

Having thus generally described the nature of the invention, reference will now be made to the accompanying drawings, showing by way of illustration, a preferred embodiment thereof, and in which:

FIGS. 4A and B illustrate that signals from the two amplifiers followers are fed-back with the help of a differential amplifier through capacitors for compensating the differential capacitance;

DETAILED DESCRIPTION OF THE PREFERRED EMBODIMENT

Figure 2:
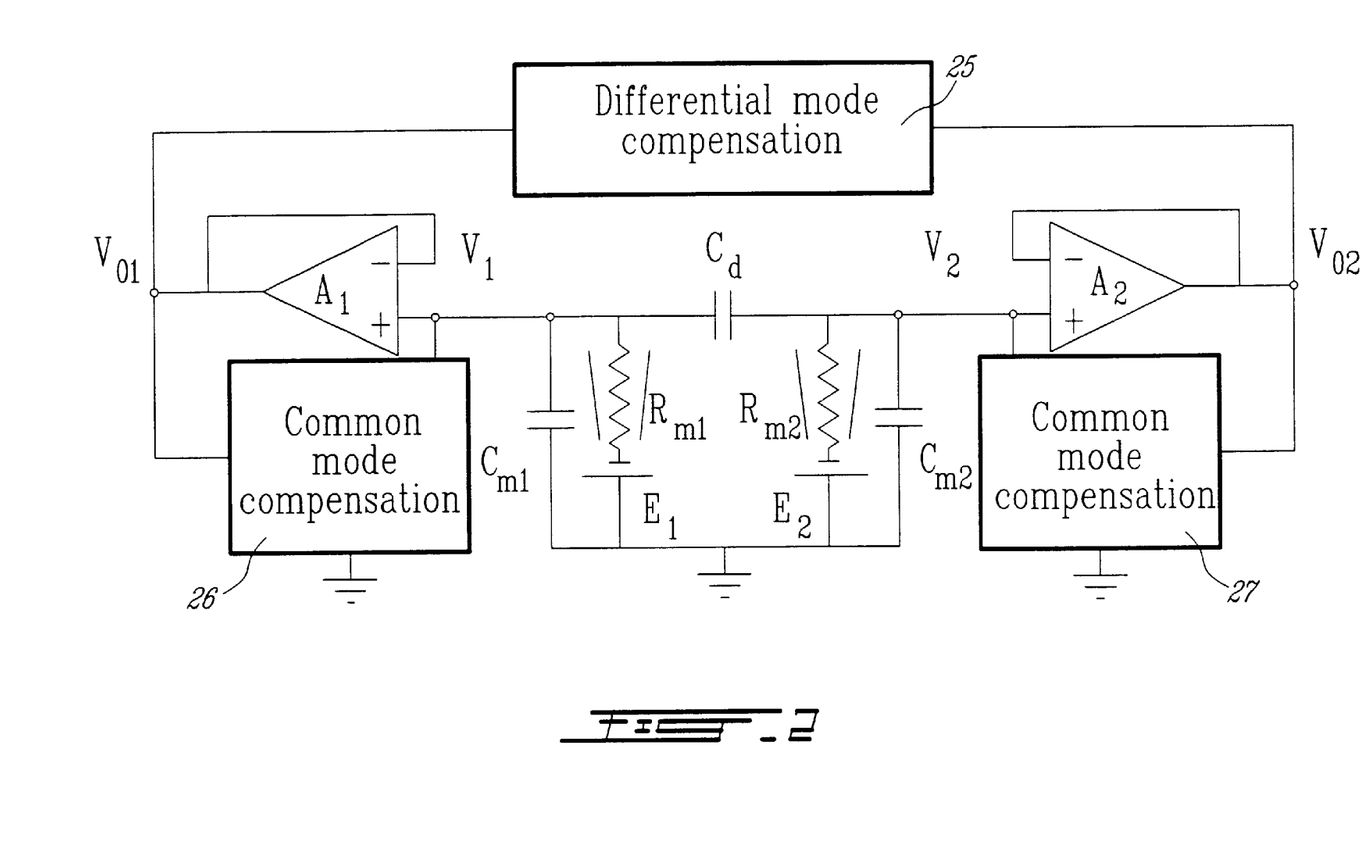
FIG. 2 illustrates the three compensation circuits needed to eliminate the undesirable stray capacitances composed of two identical circuits to compensate for the common mode capacitances and one differential mode compensation.

Three circuits are needed to compensate for the three different stray capacitances ($C_{m1}$, $C_{m2}$ and $C_d$). FIG. 2 gives an overall schematic of the proposed system. It can be shown that two identical circuits 26 and 27 compensate for each grounded capacitance $C_{m1}$ and $C_{m2}$. The third circuit 25 uses a differential mode configuration to get rid of the capacitance $C_d$. This third circuit is the main object of this invention.

Figure 3A:
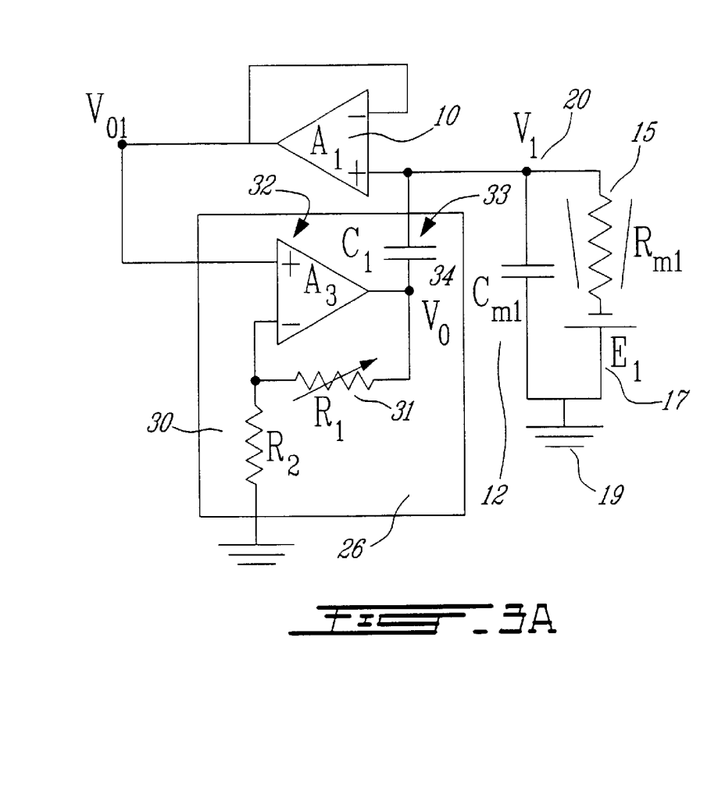
FIGS. 3A, B and C and illustrate the common mode compensation done with an amplifier which creates the proper negative capacitance.
Figure 3B:
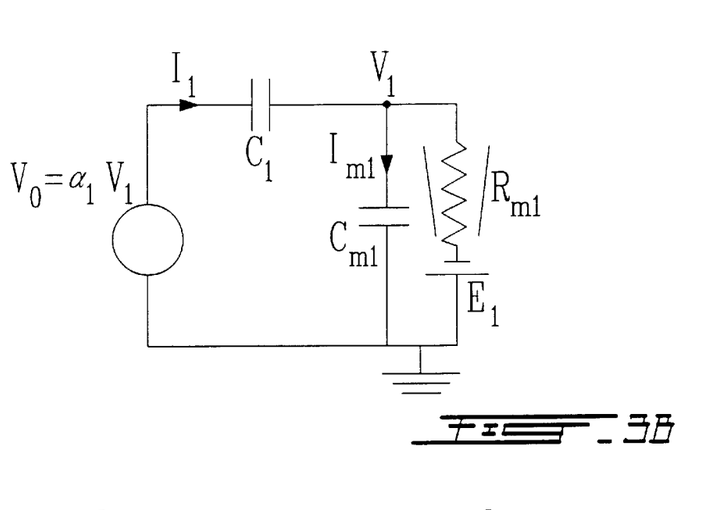
Figure 3C:
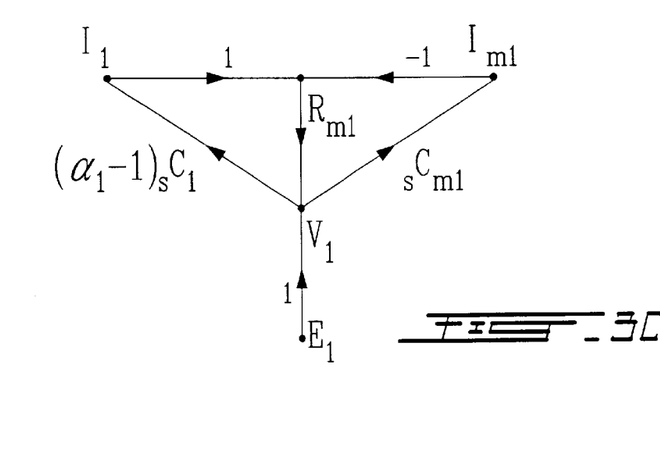

Compensating for each grounded mode capacitance (Cm1 or Cm2) is done as shown in FIG. 3 (shown here only for capacitance Cm1). This technique is known in the art. Circuit analysis (FIG. 3B and FIG. 3C) shows that voltage $V_1$ is equal to $E_1$, provided capacitors are related as: $C_{m1}=C_1(\alpha_1-1)$. The exact gain ($\alpha_1=1+R_1/R_2$) is obtained by fine tuning potentiometer resistor $R_1$. The idea is to create a negative capacitance in the positive feedback loop of amplifier A1 such that capacitance Cm1 is just cancelled out. This is done with amplifier A3 which is a follower with gain: $\alpha 1=1+R1/R2$. Assuming ideal operational amplifiers for simplicity, the resulting circuit can be analyzed as shown in FIG. 3B. The solution as a flow graph is given in FIG. 3C. The analysis is down in the complex frequency domain (s) so that capacitive admittance are written sCm1 and sC1 respectively. Perfect frequency compensation occurs provided: $Cm1=C1(\alpha 1-1)$, where $\alpha 1$ is the closed loop gain of amplifier A3. In practice, one fine-tunes R1.

Figures 4A, 4B:
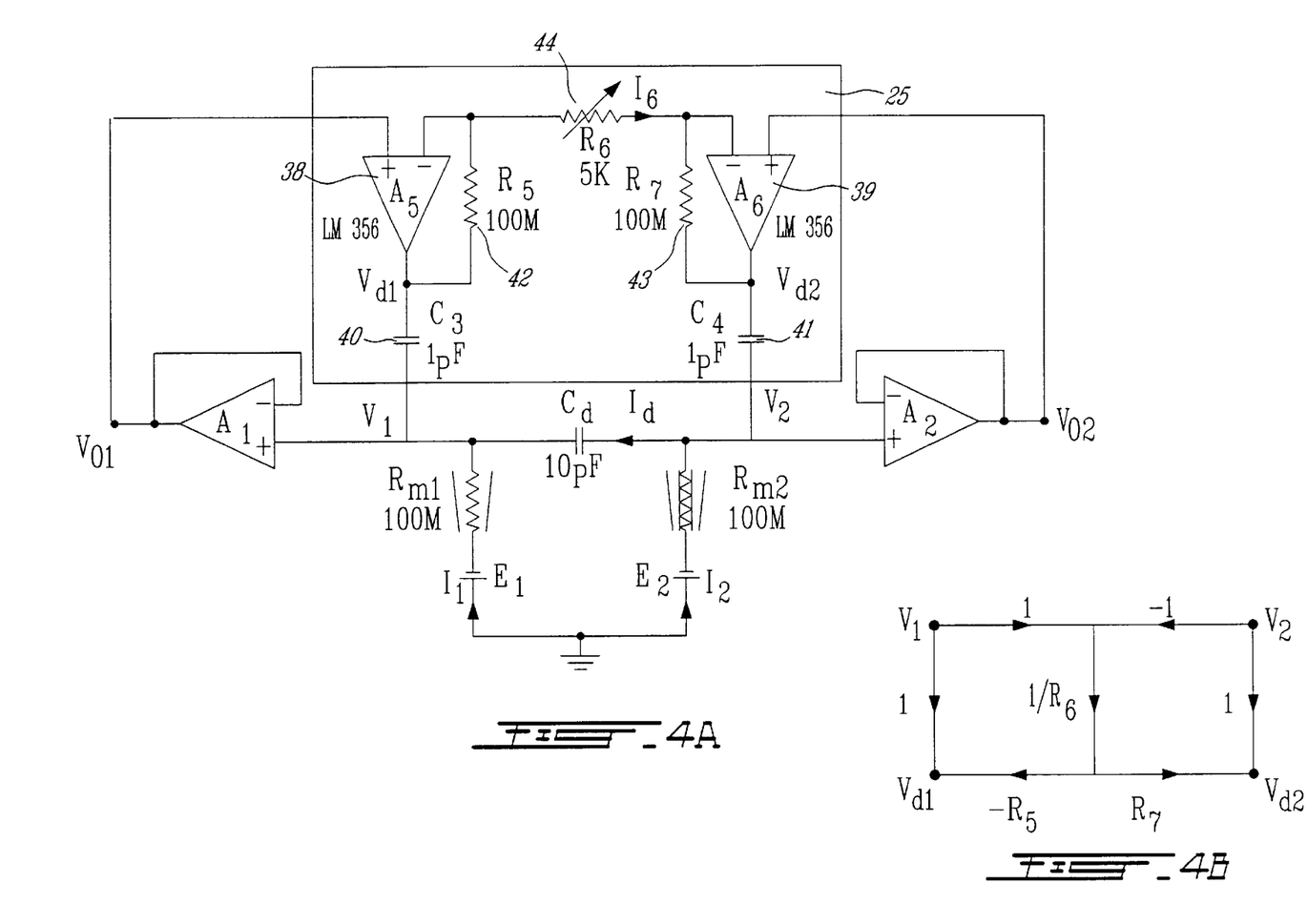

The differential capacitance ($C_d$) can be compensated by introducing a differential amplifier 25 (made of amplifiers $A_5$ and $A_6$) which is fed by the two followers ($A_1$ and $A_2$). It generates a negative differential capacitance across $C_d$ with the help of capacitors $C_3$ and $C_4$. The flow graph for the differential amplifier is given in FIG. 4. The equations that need to be respected are the following:

$$V_{d1}\alpha_2 V_1 + \alpha_3 V_2$$

$$V_{d2}\alpha_4 V_2 + \alpha_5 V_1$$

where $$\alpha_2 = (1+R5/R6)$$

$$\alpha_3 = -R5/R6$$

$$\alpha_4 = (1+R7/R6)$$

$$\alpha_5 = -R7/R6$$

Figure 5A:
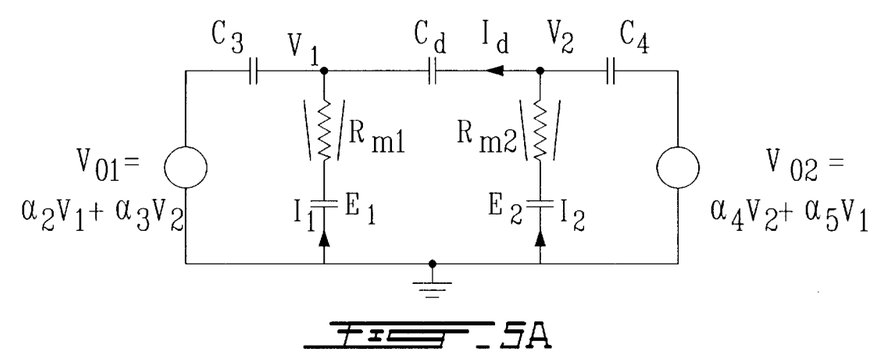
FIGS. 5A and B show the differential mode compensation circuit with the corresponding flow graph.
Figure 5B:
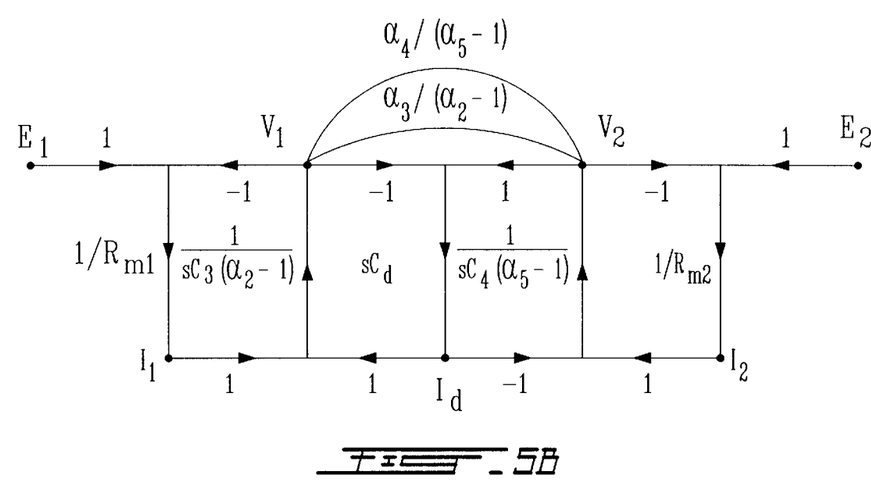

An equivalent circuit with its corresponding flow graph, for analyzing the conditions for neutralizing $C_d$, are given in FIG. 5. Each voltage source contains a $V_1$ and $V_2$ component weighted with proper gains ($\alpha_2$, $\alpha_3$, $\alpha_4$ and $\alpha_5$) for neutralizing capacitance $C_d$. It is found that capacitance neutralization ($C_d$) is achieved provided $C_d=C_3\alpha_3$. It implicitly assumes that the grounded capacitances $C_{m1}$ and $C_{m2}$ have been already neutralized. A perfect differential capacitance ($C_d$) compensation is achieved in the circuit of FIG. 4 when the recording voltages $V_1$ and $V_2$ are respectively equal to membrane potentials $E_1$ and $E_2$. The conditions required for the different gains ($\alpha_2$, $\alpha_3$, $\alpha_4$ and $\alpha_5$) and capacitors ($C_3$, $C_4$ and $C_d$) to achieve such relationships are shown below. We only prove here how to get: $V_1/E_1=1$ and $V_1/E_2=0$ (the proof: $V_2/E_2=1$ and $V_2/E_1=0$ is quite the same). It can be written from the graph of FIG. 5 that:

$$\frac{V1}{E1} = \frac{\left[1 + \frac{C_d}{C_4(1-\alpha_4)} + \frac{1}{sC_4(1-\alpha_4)R_{m2}}\right] \times \left[\frac{1}{sC_3(1-\alpha_2)R_{m1}}\right]}{\Delta}$$

Where:

$$\Delta = 1 + \frac{1}{sC_3R_{m1}(1-\alpha_2)} + \frac{C_d}{C_3(1-\alpha_2)} + \frac{C_d}{C_4(1-\alpha_4)} + \frac{1}{sC_4R_{m2}(1-\alpha_4)} + \frac{\alpha_5 C_d}{C_3(1-\alpha_2)(1-\alpha_4)} + \frac{\alpha_3 C_d}{C_4(1-\alpha_2)(1-\alpha_4)} + \frac{1}{sC_3R_{m1}(1-\alpha_2)}\left[\frac{C_d}{C_4(1-\alpha_4)} + \frac{1}{sC_4R_{m2}(1-\alpha_4)}\right] + \frac{C_d}{C_3(1-\alpha_2)}\left[\frac{1}{sC_4R_{m2}(1-\alpha_4)}\right] - \frac{\alpha_3\alpha_5}{(1-\alpha_2)(1-\alpha_4)}$$

Knowing that capacitance compensation must be done for both microelectrodes and from symmetry considerations, we write $\alpha 5=\alpha 2$ and $\alpha 4=\alpha 3$. Also, for ease of construction and without loss of generality, capacitors $C_3$ and $C_4$ and resistors $R_5$ and $R_7$ are respectively chosen of equal value. This last simplification gives: $1-\alpha 2=1-\alpha 4=\alpha 5=\alpha 3$. It follows that the preceding equation can be written as:

$$\frac{V1}{E1} = \frac{\left[1 + \frac{C_d}{C_3\alpha_3} + \frac{1}{sC_3\alpha_3 R_{m2}}\right] \times \left[\frac{1}{sC_3\alpha_3 R_{m1}}\right]}{\Delta}$$

Where:

$$\Delta = \frac{1}{sC_3R_{m1}\alpha_3}\left[1 + \frac{Cd}{C_3\alpha_3} + \frac{1}{sC_3R_{m2}\alpha_3}\right] + \frac{1}{sC_3R_{m2}\alpha_3}\left[1 + \frac{C_d}{C_3\alpha_3}\right]$$

The last term in this $\Delta$ expression can be cancelled out provided: $C_D=-C_3\alpha_3$. This condition is easily met because the gain ($\alpha_3=-R_5/R_6$) is adjustable thanks to $R_6$ (FIG. 4) which is a potentiometer. When this condition is met, differential capacitance compensation occurs. In that case, $V_1/E_1=1$ and capacitance $C_d$ is perfectly compensated.

Proceeding in a similar manner as we have just done for $V_1/E_1$, it can also be shown from the flow graph in FIG. 5 that $V_2/E_1=0$ when compensation is achieved. Indeed, from this graph, we can write:

$$\frac{V1}{E1} = \frac{\frac{1}{sC_3R_{m1}\alpha_3}\left[1 + \frac{C_d}{C_3\alpha_3}\right]}{\Delta}$$

Using the same condition for capacitance neutralization as before ($C_D=-C_3\alpha_3$), the numerator is zero and we conclude that the recorded signal ($E_1$) on microelectrode $R_{m1}$ is not seen on microelectrode $R_{m2}$ because $V_2/E_1=0$.

It is shown that floating differential capacitance ($C_d$) neutralization is achieved provided $C_d=-C_3\alpha_3=-C_4\alpha_5$, which reduces to $C_3R_7=C_4R_5$. From FIG. 4, the gain $\alpha_3$ is given by $-R_7/R_6$ and $\alpha_5$ by $-R_5/R_6$; it follows that fine tuning resistor $R_6$, which is a potentiometer, neutralizes the undesired differential capacitance $C_d$. As shown in FIG. 5, when conditions for neutralization do occur, signals $V_1$ and $V_2$ are respectively equal to the measuring voltages $E_1$ and $E_2$. No contamination or cross-talk is perceived by both microelectrodes ($V_1/E_2=0$ and $V_2/E_1=0$).

Figure 6:
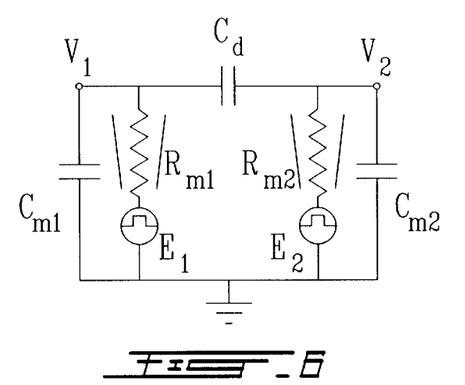
FIG. 6 illustrates a circuit representing a large cross-talk effect between two recording microelectrodes.

In order to test the proper functioning of the differential circuit, a circuit (FIG. 6) simulating severe cross-talk between two recording microelectrodes can be built. We have chosen the following values which represent typical values for this type of application. However, other values could be used without modifying the circuit. $R_{m1}=100$ M$\Omega$ and $R_{m2}=200$ M$\Omega$, $E_1$ and $E_2$ are square waves (f=10 Hz), not synchronized (out-of-phase), representing some hypothetical variable membrane voltages E1 and E2. Capacitor $C_d$ was chosen as 10 pF (a much larger value than expected in real situations) while capacitors $C_{m1}$ and $C_{m2}$ were determined according to the length of the connecting leads to the microelectrode resistors (this means they were a few pF).

In this setup, the following values were chosen for the differential amplifier: A5 and A6 are LM356, R5 and R6 are 10 K$\Omega$, C3 and C4 are 1 pF and R6 is a potentiometer of 0–5 K$\Omega$. These values have been found to be the preferred choice of components although other values could also work.

The two upper traces in FIG. 7 (FIG. 7A and FIG. 7B) are the signals measured at the output $V_{O1}$ and $V_{O2}$ of the two follower amplifiers $A_1$ and $A_2$. They show the recording signals from the circuit in FIG. 6 without capacitance compensation. Cross-talk is clearly seen between the recordings when signals $E_1$ and $E_2$ are going from low to high or high to low values. The corners are also rather rounded off. It can be seen how the up and down edges are rounded off due to stray capacitances $C_{m1}$ and $C_{m2}$. Furthermore, cross-talk is seen on both signals when voltage sources $E_1$ and $E_2$ are switching from low to high and high to low values. The voltage sources $E_1$ and $E_2$ were chosen small in order to reflect difficult recordings. Consequently, the output signals are noisy, but as seen in the lower traces, capacitance compensation does not degrade significantly the signals.

Figure 7A:
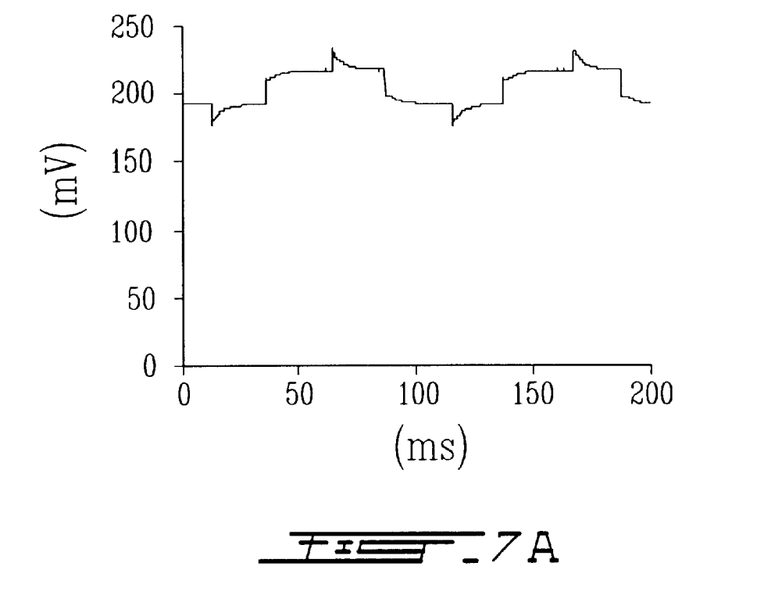
FIGS. 7A, B, C and D are illustrations of typical signals.
Figure 7B:
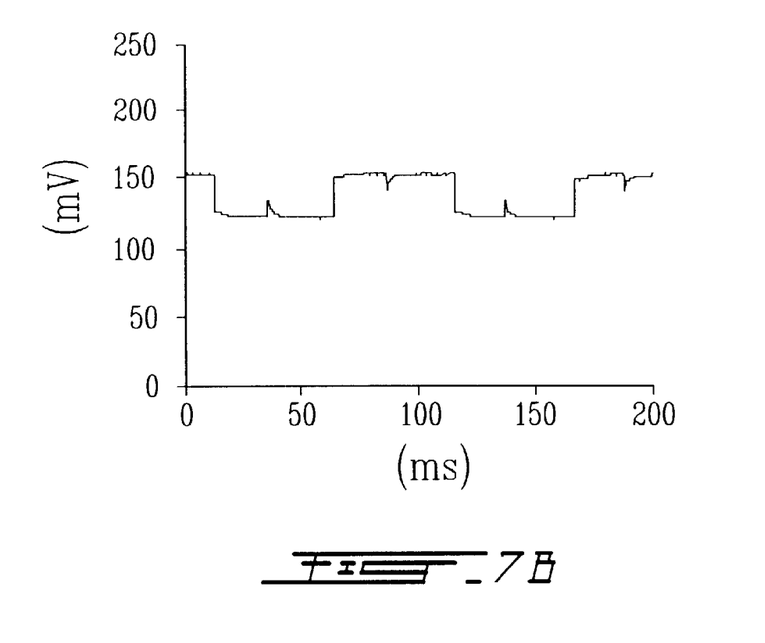
Figure 7C:
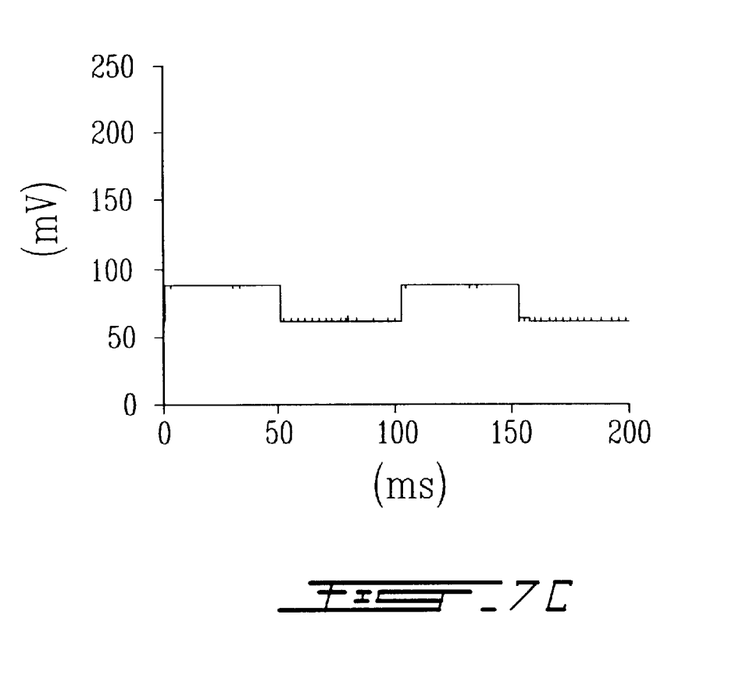
Figure 7D:
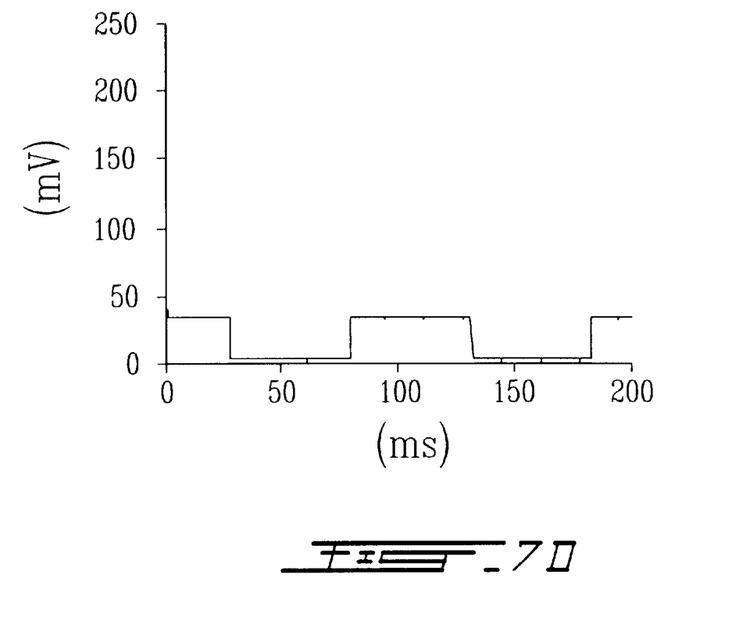

Capacitance compensation is achieved in three steps. The first two steps proceed by short circuiting alternatively the input of amplifiers $A_1$ and $A_2$ for compensating capacitances $C_{m1}$ and $C_{m2}$ respectively. This is done by fine tuning resistors $R_1$ and $R_3$ (see FIG. 3 for $R_1$; the circuit for $R_3$ (not shown) is identical to the one in FIG. 3). Compensation for the floating capacitance $C_d$ is done by fine tuning potentiometer $R_6$ (FIG. 4). The two bottom traces in FIG. 7 (FIG. 7C and FIG. 7D) show how good the compensation is for all stray capacitances. The square waves can be seen to be reproduced without rounding and mutual cross-talk effects.

What makes the proposed circuit interesting is that it achieves a perfect symmetrical compensation. Any action on one microelectrode is not perceived by the other one. Any microelectrode can be the injecting one or the recording one, and both can be recording. Any transient effect on one microelectrode is not reflected as cross-talk on the other one. Without differential compensation, there is no way to correct the recorded signals because their real time course is unknown. A look at the experimental results illustrated in FIG. 7 shows how important differential compensation is for recovering the signal without distorted effects.

We claim:

1. A method for processing signals from two microelectrodes to neutralize a floating differential capacitance between said two microelectrodes, comprising: detecting, using a first microelectrode, a first electrical potential at a first point from an organism;

detecting, using a second microelectrode, a second electrical potential at a second point from said organism, said floating differential capacitance appearing between said first and second electrodes;

providing an adjustable differential amplifier;

connecting said differential amplifier to said first and second potentials generating a negative differential capacitance using said differential amplifier across said floating differential capacitance;

adjusting said negative differential amplifier to neutralize said floating differential capacitance.

2. A method as claimed in claim 1, wherein said providing step comprises providing two amplifiers inter-connected by an adjustable resistive element.

3. A method as claimed in claim 1, wherein said connecting step comprises connecting the differential amplifier through capacitors.

4. A method as claimed in claim 2, wherein said adjusting step comprises adjusting said resistive element.

5. A method as claimed in claim 1, wherein said adjusting comprises displaying the potential measured and making a manual adjustment on the adjustment circuit element.

6. A method as claimed in claim 1, wherein said adjusting comprises analyzing a waveform of the potentials and providing said differential amplifier with an adjustment.

7. A system for synthesizing a negative floating capacitance matching a floating differential capacitance appearing between two microelectrodes, comprising:

a first amplifier having a positive input connected to an output of a first microelectrode;

a second amplifier having a positive input connected to an output of a second microelectrode;

an adjustment circuit element interconnecting negative inputs of said first and second amplifiers to adjust said negative floating capacitance;

said first and second amplifiers having outputs connected to said outputs of said first and second microelectrodes, whereby providing a negative floating capacitance matching said floating differential capacitance.

8. A system as claimed in claim 7, wherein said output of said first microelectrode goes through a first follower amplifier and said output of said follower is connected to said positive input of said first amplifier and said output of said second microelectrode goes through a second follower amplifier and said output of said second follower is connected to said positive input of said second amplifier.

9. A system as claimed in claim 7, wherein said adjustment circuit element is a variable resistive element.

10. A system as claimed in claim 7, wherein said outputs of said first and second amplifiers are connected to capacitive elements, said capacitive elements being connected to said outputs of said microelectrodes.

11. A system as claimed in claim 7, further comprising an oscilloscope for displaying signals of said microelectrodes.

12. A system as claimed in claim 7, further comprising an analyzer for waveforms of the outputs of said microelectrodes, whereby adjusting said adjustment circuit element.

* * * * *

UNITED STATES PATENT AND TRADEMARK OFFICE
CERTIFICATE OF CORRECTION

PATENT NO.     : 6,385,019 B1
DATED          : May 7, 2002
INVENTOR(S)    : Gagné et al.

It is certified that error appears in the above-identified patent and that said Letters Patent is hereby corrected as shown below:

<u>Title page,</u>
Item [75], Inventor, "Ganguly's" first name should read -- Udaya -- and not "Jdaya".

Signed and Sealed this

Fourth Day of February, 2003

JAMES E. ROGAN
*Director of the United States Patent and Trademark Office*